(12) United States Patent
Ho et al.

(10) Patent No.: US 12,623,051 B2
(45) Date of Patent: May 12, 2026

(54) DRAINAGE DEVICE

(71) Applicants: Chung-Yung Ho, Taipei City (TW);
Chung-Chen Ho, Taipei City (TW);
Hong-Fa Ho, Taipei City (TW)

(72) Inventors: Chung-Yung Ho, Taipei City (TW);
Chung-Chen Ho, Taipei City (TW);
Hong-Fa Ho, Taipei City (TW)

( * ) Notice: Subject to any disclaimer, the term of this patent is extended or adjusted under 35 U.S.C. 154(b) by 464 days.

(21) Appl. No.: 18/499,779

(22) Filed: Nov. 1, 2023

(65) Prior Publication Data

US 2025/0050057 A1      Feb. 13, 2025

(30) Foreign Application Priority Data

Aug. 7, 2023    (TW) ................................. 112129602

(51) Int. Cl.
*A61M 25/00* (2006.01)
*A61M 25/10* (2013.01)
*A61M 39/26* (2006.01)

(52) U.S. Cl.
CPC .. *A61M 25/0017* (2013.01); *A61M 25/10185* (2013.11); *A61M 39/26* (2013.01); *A61M 2210/1078* (2013.01)

(58) Field of Classification Search
CPC ........ A61M 25/0017; A61M 25/10178; A61M 39/26; A61M 2210/1078
See application file for complete search history.

(56) References Cited

U.S. PATENT DOCUMENTS

| | | | |
|---|---|---|---|
| 10,010,392 B1* | 7/2018 | Zukowski | A61F 2/0009 |
| 11,752,302 B1* | 9/2023 | Zukowski | A61M 25/0075 604/544 |
| 12,251,522 B1* | 3/2025 | Chen | A61M 25/04 |
| 2002/0045855 A1* | 4/2002 | Frassica | A61B 1/00148 604/103.08 |
| 2005/0101941 A1* | 5/2005 | Hakky | A61M 25/0017 604/544 |
| 2010/0312225 A1* | 12/2010 | Armistead | A61M 25/0075 606/108 |
| 2020/0384241 A1* | 12/2020 | Herrera | A61B 5/204 |
| 2022/0370180 A1* | 11/2022 | Kadron | A61M 25/0017 |
| 2023/0173246 A1* | 6/2023 | Takiguchi | A61M 25/0017 604/544 |
| 2024/0130843 A1* | 4/2024 | Howes | A61M 25/0017 |

* cited by examiner

*Primary Examiner* — Philip R Wiest
(74) *Attorney, Agent, or Firm* — Guice Patents PLLC

(57) ABSTRACT

A drainage device having a catheter and a control valve, the control valve having a valve body and a resilient switch controlling the valve body, the valve body being connected to the catheter, the resilient switch being provided in the catheter, and characterized in that: the user can deform the resilient switch to adjust the opening of the valve body by pressing the catheter or pressing a body part having a cavity accommodating the catheter, and can further compel the resilient switch into a recovery-blocked status; and the user can release the recovery-blocked status by bending or shaking the catheter or bending or shaking the body part accommodating the catheter.

10 Claims, 14 Drawing Sheets

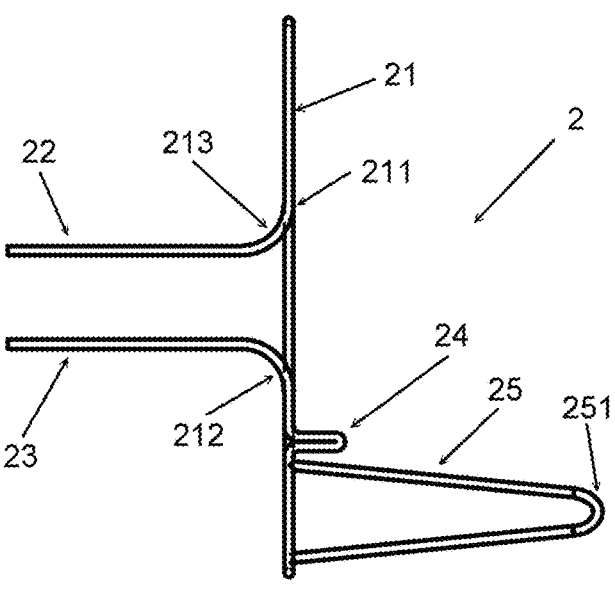
FIG. 3
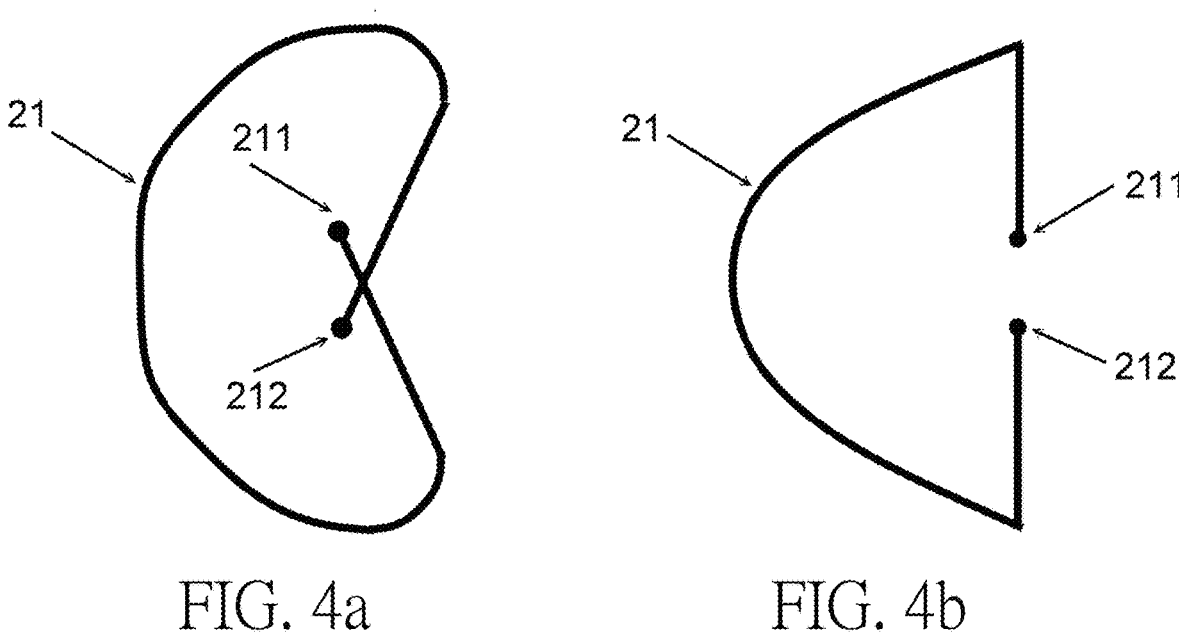
FIG. 4a                    FIG. 4b

DRAINAGE DEVICE

BACKGROUND OF THE INVENTION

Field of the Invention

The present invention relates to a drainage device, in particular to a medical drainage device.

Description of the Related Art

There are different types of drainage devices. In the type of drainage device having a control valve, the passageway thereof can be controlled by the control valve to be normally closed, normally open, or in a variable open status adjusted by a pressing force acting on the control valve.

Drainage devices can be used before, during and after a surgery in hospital, or for self-catheterization in daily life. There are a variety of drainage devices: for example, intravenous drip line, pigtail catheters or chest tube for thoracentesis drainage, wound draining tube for draining blood, water, secretions, or fluid accumulated in a cavity, urinary catheter for males having urinary difficulty with or without benign prostatic hyperplasia (BPH), urinary incontinence, urinary retention, or repeated urinary tract infections. Besides, there are also indwelling urinary catheter and intermittent urinary catheter used as a replacement means or temporary means for the treatment of BPH.

In some cases, the urinary catheter needs to be drainage controllable for patients with urinary retention, patients with compromised urinary sphincter function due to implantation of a prosthetic stent, bladder neck stent or catheter, or being under anesthesia, or patients with urinary incontinence.

However, for the urinary catheter to be fully retained in the body, conventional urinary catheters still lack a convenient way for adjusting the drainage path thereof.

In addition, as the valve used in most conventional controllable drainage devices is generally composed of many parts and complex in structure, the manufacturing cost thereof is inherently high and there remains room for improvement.

To solve the problems mentioned above, a novel drainage device is needed in the field.

SUMMARY OF THE INVENTION

The main objective of the invention is to propose a drainage device having a catheter, which, by installing a resilient switch in the catheter, a user can deform the resilient switch to adjust the opening of a valve connected with the catheter by pressing the catheter or pressing a body part having a cavity accommodating the catheter, and can further compel the resilient switch into a recovery-blocked status; and the user can release the recovery-blocked status by bending or shaking the catheter, or bending or shaking the body part accommodating the catheter.

That is, the drainage device of the invention not only allows a user to manually press a resilient switch hidden in a catheter to adjust the opening of the valve, but also allows the user to perform a bending or shaking operation to release the resilient switch hidden in the catheter from a recovery-blocked status to make the resilient switch resiliently restored to an initial state.

To attain the foregoing objective, a drainage device is proposed, which includes a catheter and a control valve connected with the catheter, characterized in that:

the control valve has a valve body and a resilient switch, the valve body having a passageway controlled by the resilient switch to be in a normally closed status, a normally open status, or a variable open status adjusted by a pressing force acting on the resilient switch; and the resilient switch includes an elastic structure, a driving part, a recovery-blocking part and an unlocking handle, where the driving part is movable by a deformation response of the elastic structure to have a displacement to alter an opening of the passageway of the valve body; the recovery-blocking part is used for providing a recovery-blocking effect on the driving part; and the unlocking handle is used for an external force to apply a moment of force on the driving part to release the recovery-blocking effect;

where, when the elastic structure is not pressed, the passageway is in a first normal status; when the elastic structure is under a press operation, the opening of the passageway is determined according to a relative relationship between the displacement and a displacement threshold, where, when the displacement is not larger than the displacement threshold, the passageway is in the variable open status, and the opening thereof is smaller than the opening of the normally open status, and when the displacement is larger than the displacement threshold, the driving part will be under the recovery-blocking effect provided by the recovery-blocking part to make the passageway situated in a second normal status, where, when the first normal status is the normally closed status, the second normal status is the normally open status, and when the first normal status is the normally open status, the second normal status is the normally closed status; and after the passageway is in the second normal status, the unlocking handle can be used to release the recovery-blocking effect of the recovery-blocking part by applying the moment of force, thereby restoring the passageway to the first normal status.

In one embodiment, the moment of force is generated by a bending operation or shaking operation acting on the catheter.

In one embodiment, the catheter is to be placed into a cavity to provide a flow controllable draining function.

In one embodiment, the catheter has a fixation structure for fixing the catheter in the cavity.

In one embodiment, the fixation structure includes at least one channel formed in a shell of the catheter and a balloon connected with the at least one channel, where the catheter is fixed in the cavity by introducing a volume of a fluid into the balloon via the at least one channel to inflate the balloon.

For possible embodiments, the fluid can be a gas or a liquid.

In one embodiment, the catheter has an engagement structure disposed on an inner surface of the shell of the catheter for fixing the elastic structure.

For possible embodiments, the valve body can be a duckbill valve, a gate valve, a butterfly valve, a ball valve, a plunger valve, a plug valve, or a diaphragm valve.

In one embodiment, the flow controllable draining function is for draining a body fluid in some cavity of animals.

In one embodiment, the body fluid is urine.

BRIEF DESCRIPTION OF THE DRAWINGS

FIG. 3 shows an illustrative drawing of a resilient switch of the drainage device of FIG. 1.

FIG. 4*a* shows an illustrative drawing of an embodiment of an elastic structure of the resilient switch of FIG. 1.

FIG. 4*b* shows an illustrative drawing of another embodiment of an elastic structure of the resilient switch of FIG. 1.

DETAILED DESCRIPTION OF THE PREFERRED EMBODIMENTS

Figure 1:
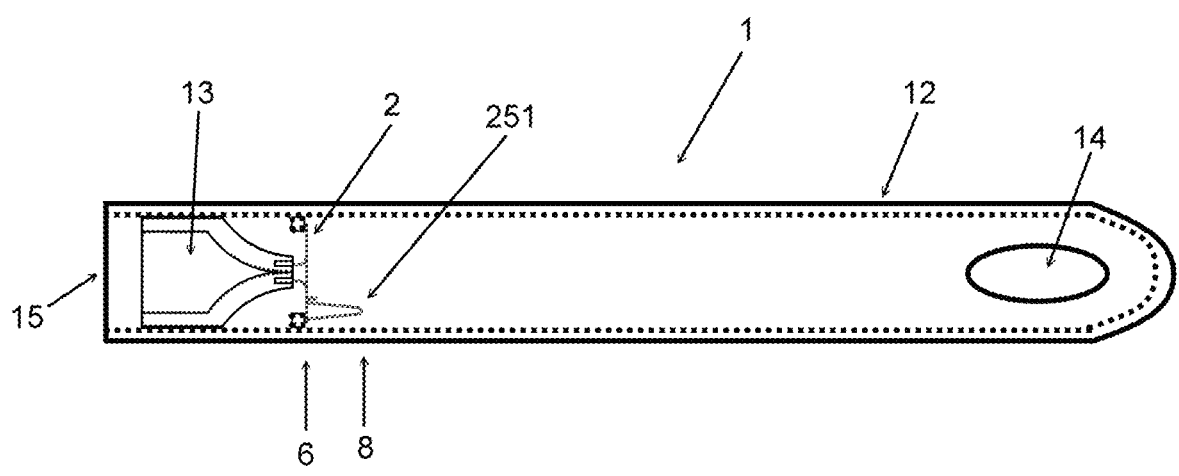
FIG. 1 shows an illustrative drawing of a drainage device according to one embodiment of the present invention.

Please refer to FIG. 1, which shows an illustrative drawing of a drainage device according to one embodiment of the present invention. As illustrated in FIG. 1, a drainage device 1 includes a catheter 12 and a control valve connected with the catheter 12, where the control valve includes a resilient switch 2 and a valve body 13, the valve body 13 has a passageway controlled by the resilient switch 2 to be in a normally closed status, a normally open status, or a variable open status adjusted by a pressing force acting on the resilient switch 2.

The catheter 12 has an inlet 14 and an outlet 15, where the inlet 14 is for introducing a fluid into the catheter 12, and the outlet 15 is for discharging the fluid. Besides, the valve body 13 is connected with the catheter 12 to form a passageway for the fluid to flow through, where the valve body 13 can be completely hidden in the catheter 12 as shown in FIG. 1, or partially hidden in the catheter 12.

It is to be noted that after the control valve is installed in the catheter 12 at a first position 6, a tip 251 of an unlocking handle of the resilient switch 2 is at a second position 8, and the catheter 12 is flexible at the first position 6 and the second position 8.

Figure 2:
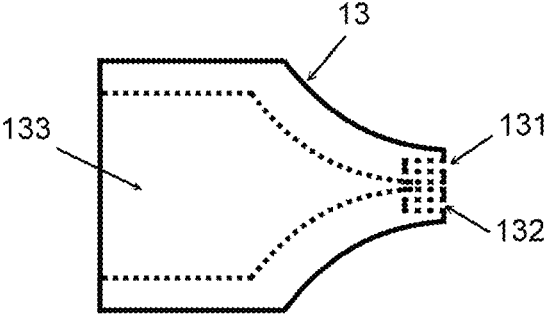
FIG. 2 shows an illustrative drawing of a valve of the drainage device of FIG. 1.

The valve body 13 is used for controlling the flow of the fluid and can be a duckbill valve, a gate valve, a butterfly valve, a ball valve, a plunger valve, a plug valve, or a diaphragm valve. FIG. 2 shows an illustrative drawing of a duckbill valve, which includes a pair of elastic lips (131, 132) and a valve path 133, where the elastic lips (131, 132) are under the control of the resilient switch 2 to determine the effective opening of the valve path 133.

Please refer to FIG. 3, which shows an illustrative drawing of the resilient switch 2. As shown in FIG. 3, the resilient switch 2 includes an elastic structure 21, a driving part including a pair of driving arms (22, 23), a recovery-blocking part 24 and an unlocking handle 25, where the driving arms (22, 23), the recovery-blocking part 24 and the unlocking handle 25 are all connected with the elastic structure 21; the driving arm 22 is protruding from a first free end 211 of the elastic structure 21, and the driving arm 23 is protruding from a second free end 212 of the elastic structure 21; and the driving arm 22 has a corner 213 connected with the elastic structure 21 for engagement with the recovery-blocking part 24. The resilient switch 2 is connected with the valve body 13 by having the driving arms (22, 23) engaged with the elastic lips (131, 132). The driving arms (22, 23) can be engaged with the elastic lips (131, 132) in two ways, as shown in FIG. 4*a* and FIG. 4*b* respectively, to make the passageway of the valve body 13 situated in the normally closed status or the normally open status.

The operation principle of the resilient switch 2 configured as shown in FIG. 4*a* to make the passageway of the valve body 13 situated in the normally closed status will be elaborated below, and as the operation principle of the resilient switch 2 configured as shown in FIG. 4*b* to make the passageway of the valve body 13 situated in the normally open status is basically the same as that of the resilient switch 2 configured as shown in FIG. 4*a*, it will not be addressed.

Figure 4C:
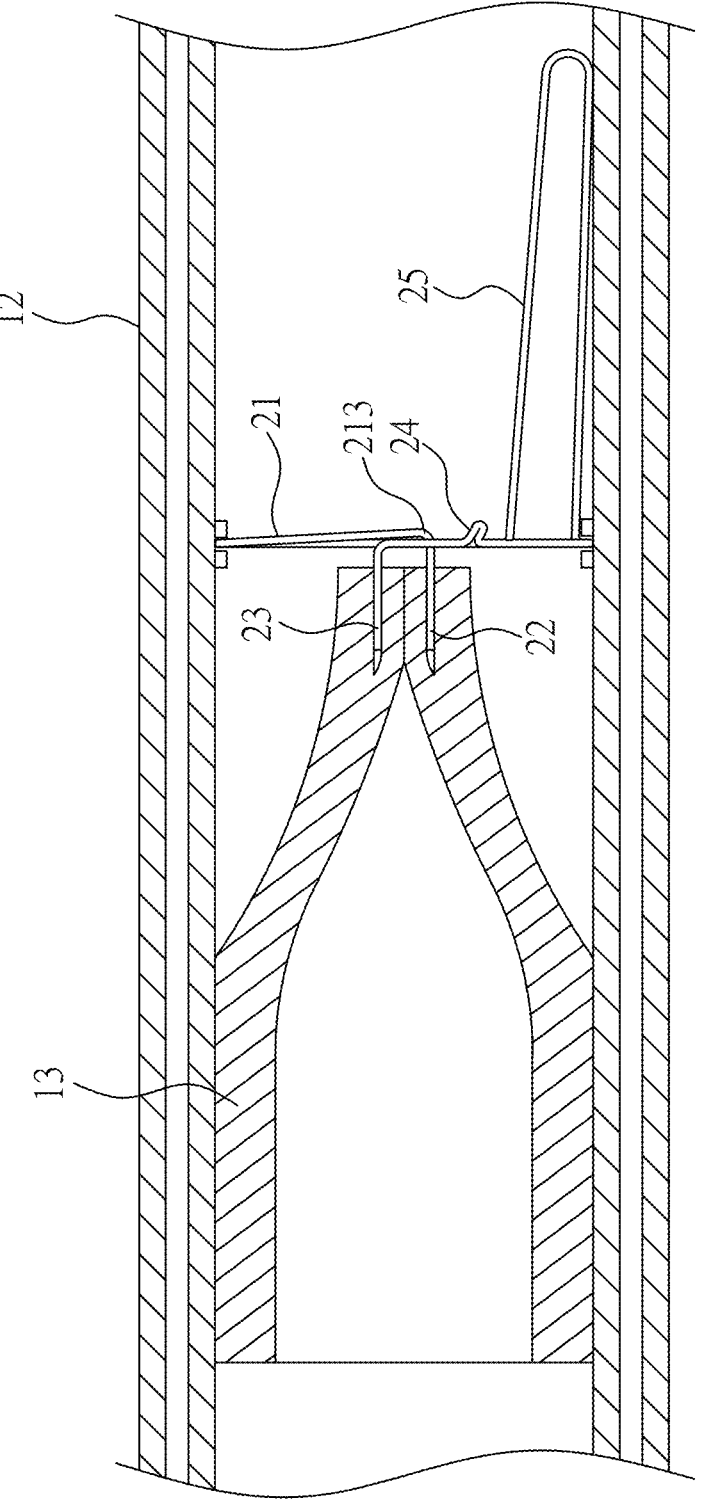
FIG. 4*c* illustrates a partial view of the drainage device of FIG. 1.

When the driving arms (22, 23) are engaged with the elastic lips (131, 132) in the way to make the passageway of the valve body 13 situated in the normally closed status, as can be seen from FIG. 4*a*, the first free end 211 and the second free end 212 are resiliently crossed over to make the driving arms (22, 23) driven by a recovery force of the elastic structure 21 to compress the elastic lips (131, 132) to effectively close the passageway of the valve body 13, and the scenario can be seen in FIG. 4*c*, where the valve body 13 is compressed to be tightly closed by the driving arms (22, 23) driven by a recovery force of the elastic structure 21.

Figure 4D:
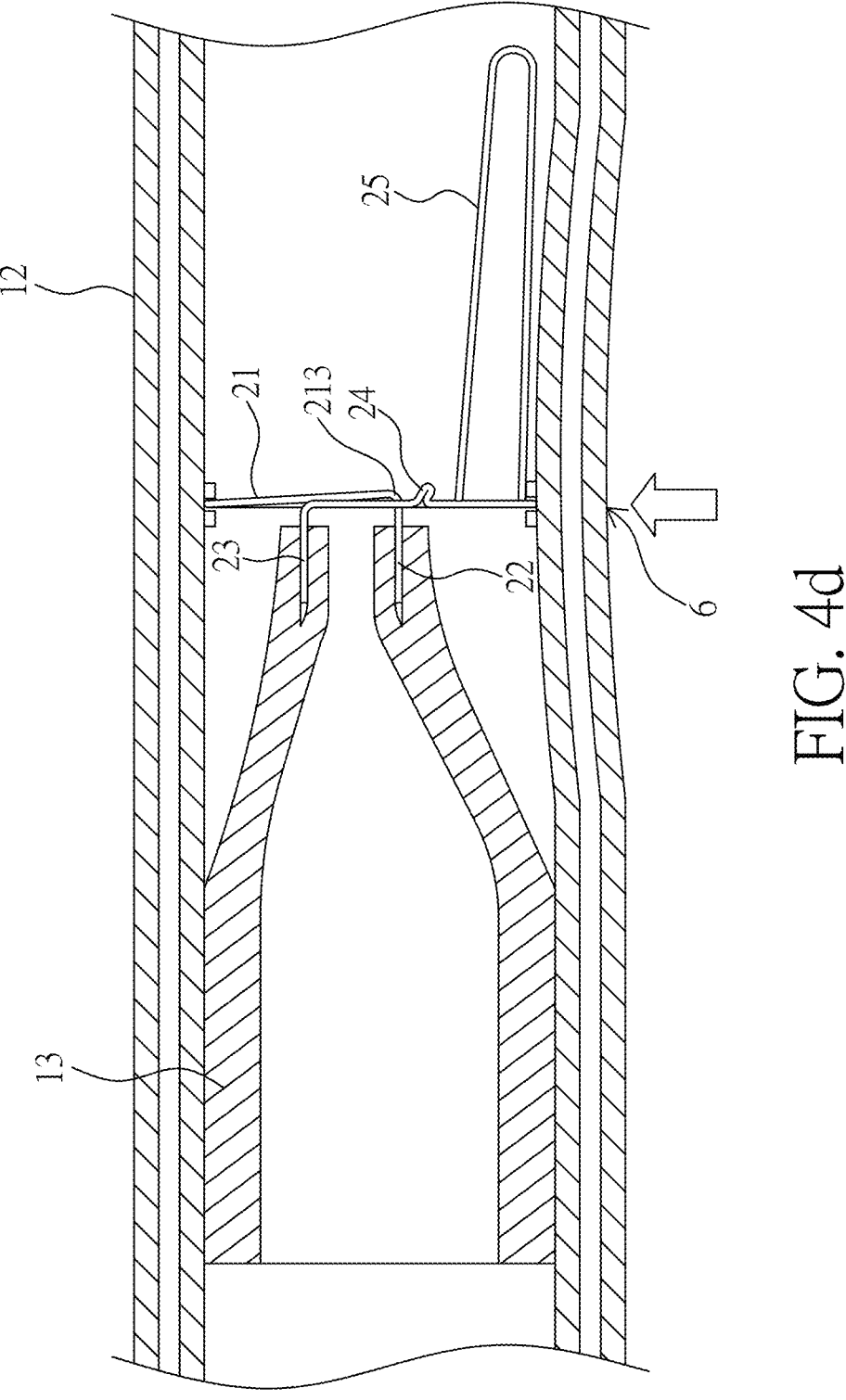
FIG. 4*d* illustrates an open status of the resilient switch of FIG. 1 caused by a pressing force acting on the resilient switch.
Figure 4E:
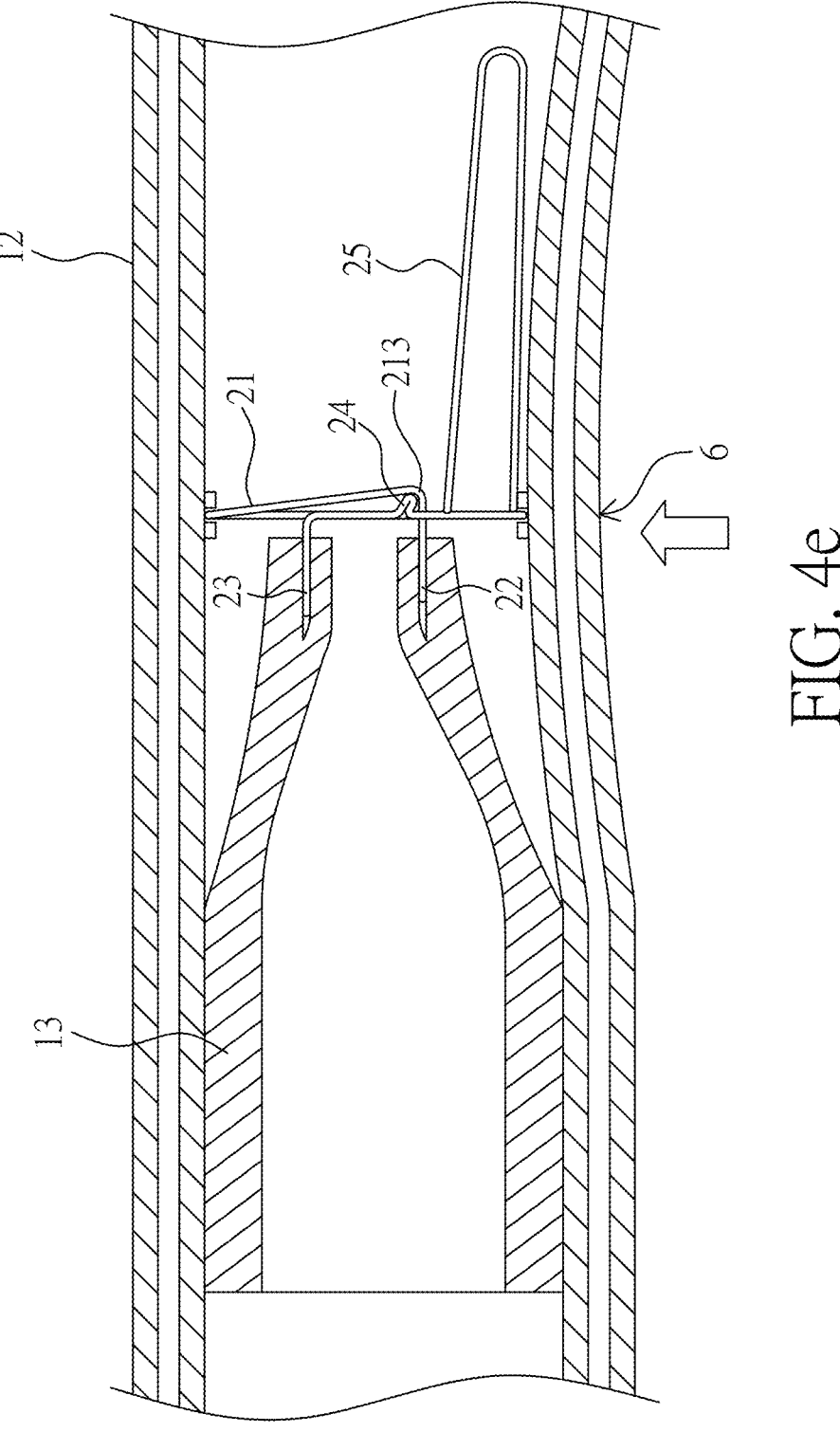
FIG. 4*e* illustrates a further open status of the resilient switch of FIG. 1 caused by a pressing force acting on the resilient switch.
Figure 4F:
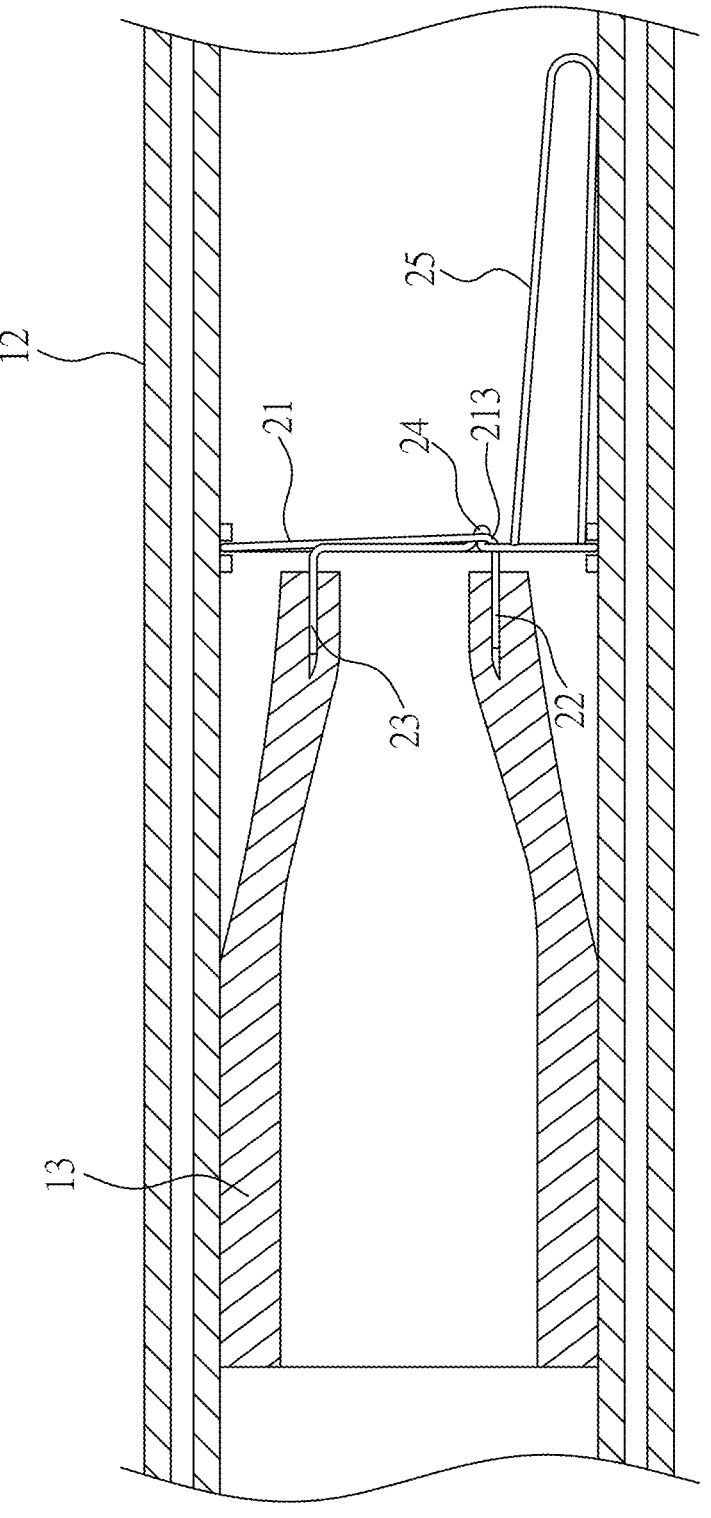
FIG. 4*f* illustrates a normally open status of the resilient switch of FIG. 1.
Figure 4G:
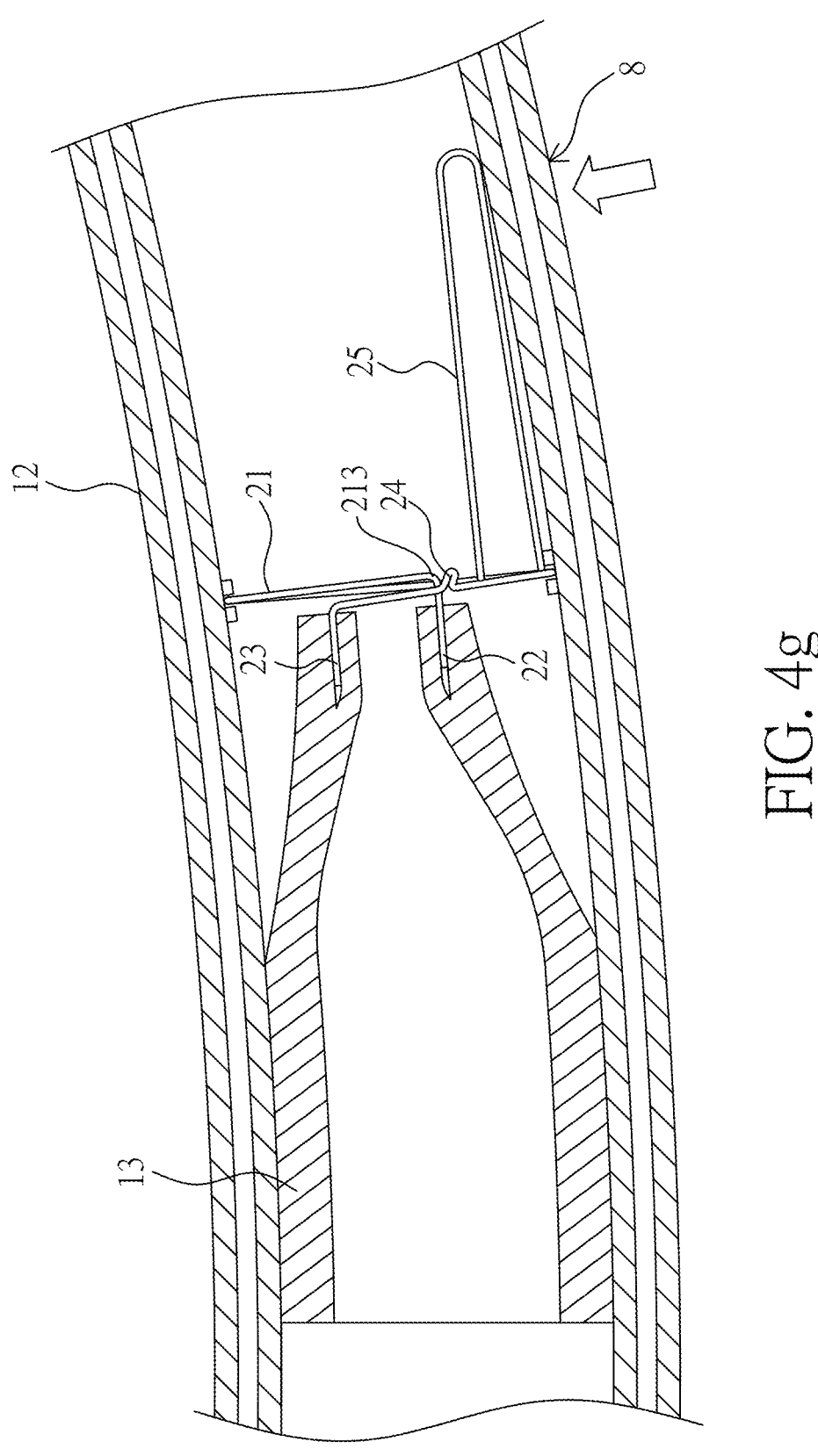
FIG. 4*g* illustrates a scenario where the resilient switch of FIG. 1 is released from the normally open status by a moment of force caused by a bending force acting on the resilient switch.

In addition, when the drainage device 1 is pressed by an external force at the first position 6, the elastic structure 21 is deformed to move the driving arms (22, 23) apart, as can be seen form FIG. 4*d*; when the drainage device 1 is further pressed by the external force at the first position 6 so that the driving arms (22, 23) are further separated to have the corner 213 passing the recovery-blocking part 24, as can be seen form FIG. 4*e*, the opening of the passageway of the valve body 13 reaches a maximum width, and after the pressing force is released, the corner 213 will be engaged with the recovery-blocking part 24 and blocked by a protruding feature of the recovery-blocking part 24 to maintain the maximum width of the opening of the passageway, as can be seen from FIG. 4*f*; and after the opening of the passageway is locked in the maximum width, the user can apply an unlocking force at or near the second position 8 of the catheter 12 to generate a moment of force via the unlocking handle 25 to release the corner 213 from being blocked by the recovery-blocking part 24, as can be seen from FIG. 4g, thereby restoring the passageway to the initial status. Besides, the unlocking force can be resulted from a bending operation or a shaking operation.

Figure 5:
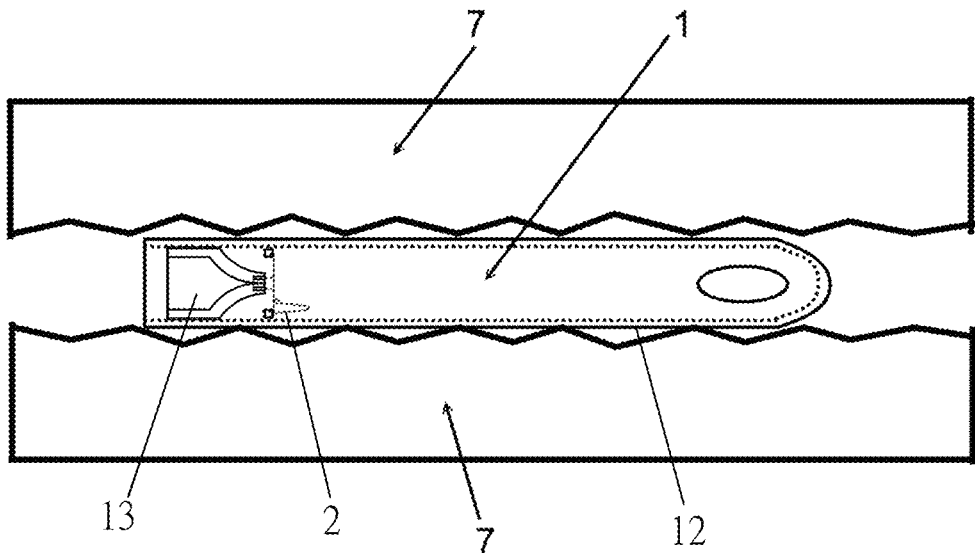
FIG. 5 illustrates a scenario where the drainage device of FIG. 1 is placed in a cavity of a chamber.

Please refer to FIG. 5, which illustrates a scenario where the drainage device 1 is placed in a cavity of a chamber 7. The chamber 7 can be a biological chamber or an artificial chamber. It is to be noted that although the drainage device 1 is completely hidden in the chamber 7 in FIG. 5, it can also be partially hidden in the chamber. When the drainage device 1 is completely hidden in the chamber 7, the user can press the outer surface of the chamber 7 to deform the resilient switch 2 to adjust the opening of the valve body, and can further compel the resilient switch 2 into a recovery-blocked status; and the user can release the recovery-blocked status by bending or shaking the chamber 7.

When the drainage device 1 is partially hidden in the chamber 7 to leave the resilient switch outside the chamber 7, the user can press the catheter to deform the resilient switch 2 to adjust the opening of the valve body, and can further compel the resilient switch 2 into a recovery-blocked status; and the user can release the recovery-blocked status by bending or shaking the catheter.

Figure 6:
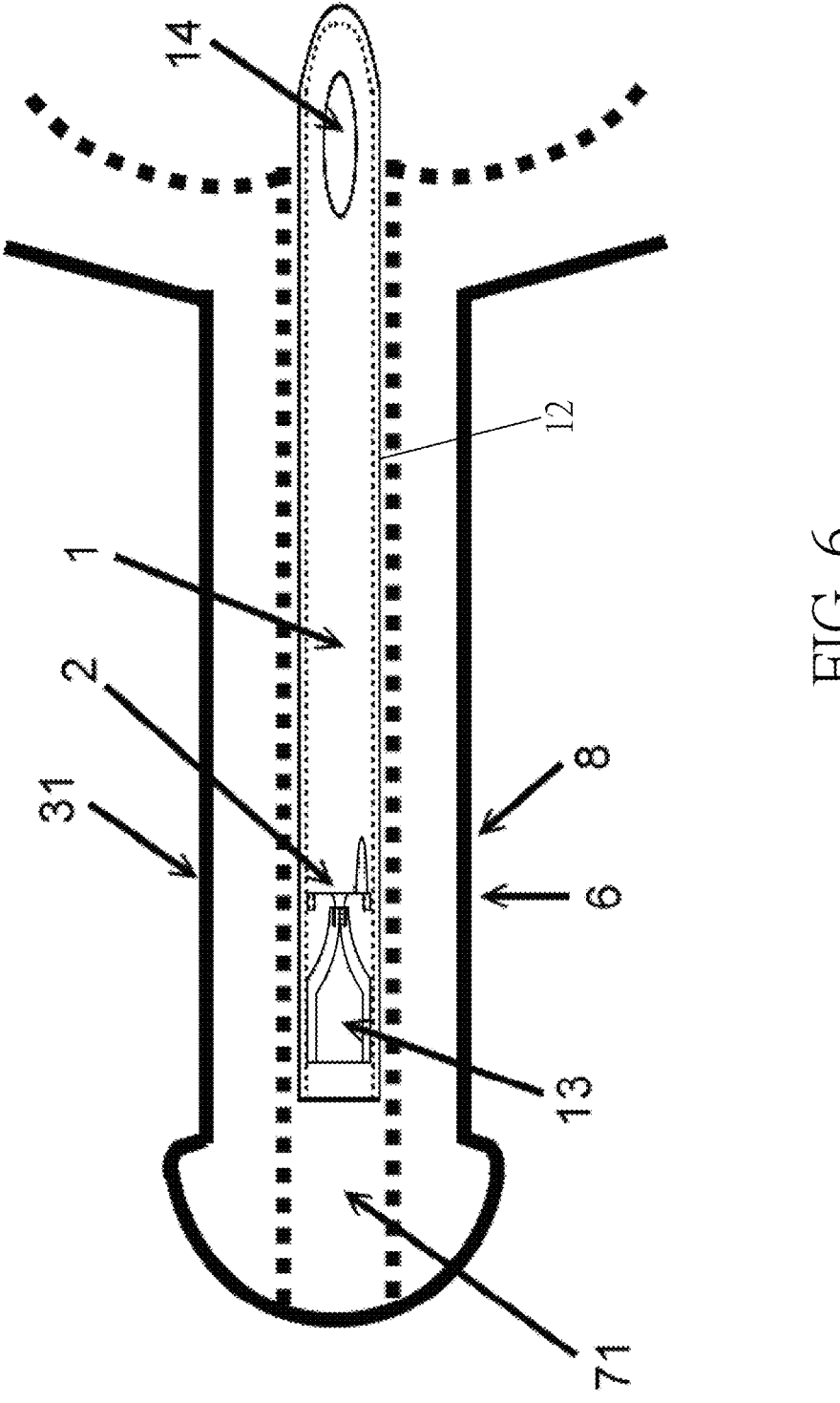
FIG. 6 illustrates a scenario where the drainage device of FIG. 1 is placed in a urethra of a male.

Please refer to FIG. 6, which illustrates a scenario where the drainage device 1 is placed in a urethra of a male. As illustrated in FIG. 6, the drainage device 1 is inserted through a urethra 71 of a penis 31 to a bladder, where the inlet 14 is located in the bladder for allowing urine to flow in the catheter of the drainage device 1.

When in use, the user can press the outer surface of the penis 31 at the first position 6 to deform the resilient switch 2 to adjust the opening of the valve body 13 to allow a urine flow, and can further compel the resilient switch 2 into a recovery-blocked status to maintain a maximum of the urine flow; and the user can release the recovery-blocked status by bending or shaking the penis 31 at the second position 8 to close the opening of the valve body 13, thereby inhibiting the urine flow.

In addition, the spring constant of the elastic structure 21 can be selected to determine a suitable leakage pressure threshold of the closure of the elastic lips (131, 132) to provide an auto-urine-leakage mechanism to prevent over-inflation of the bladder. Besides, the length of the unlocking handle 25 can be properly selected to facilitate the bending operation or shaking operation to release the recovery-blocked status. Moreover, the catheter 12 can widen the opening of the urethra of a BPH patient when inserted into the prostate area of the BPH patient.

Figure 7:
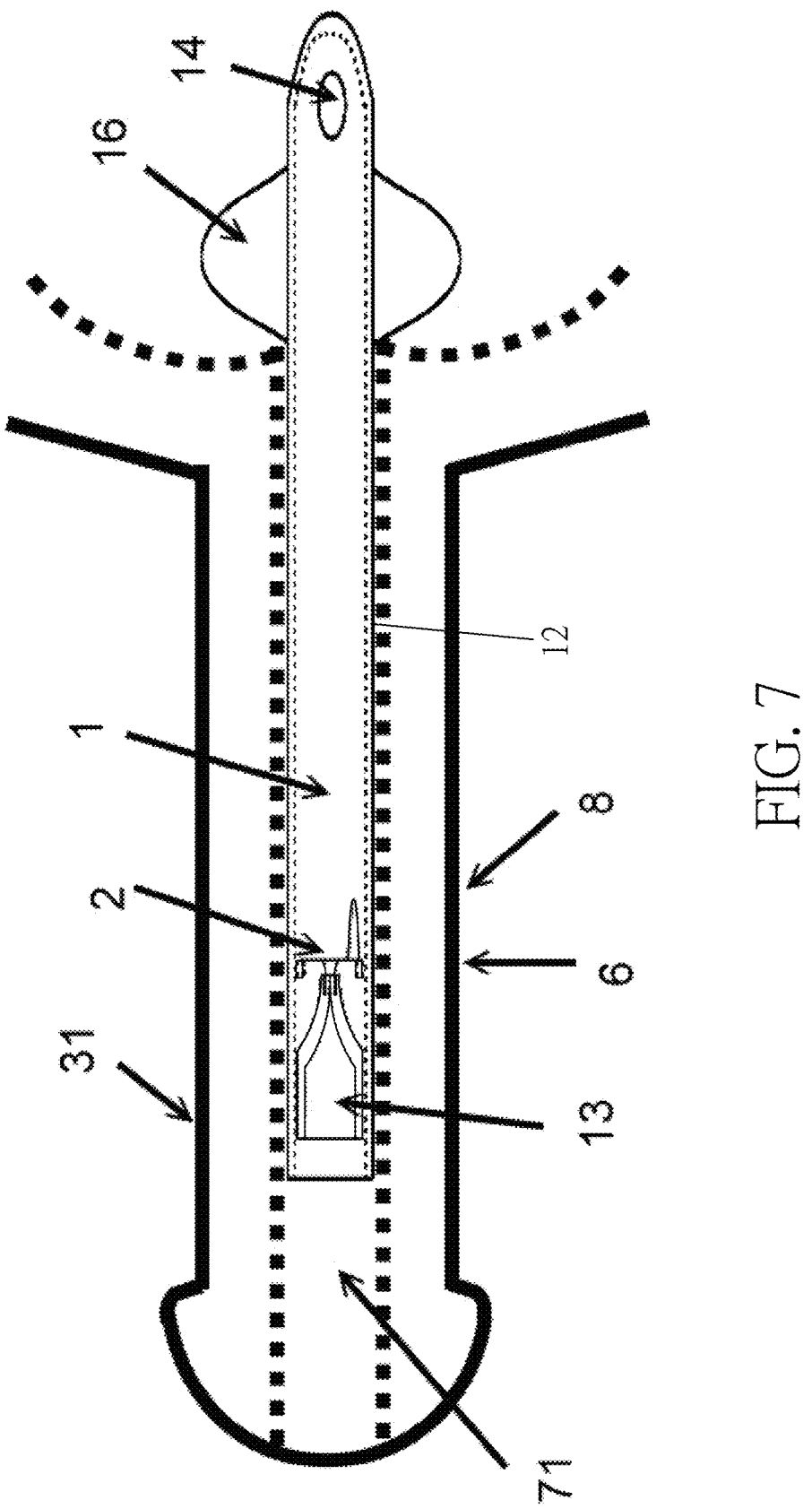
FIG. 7 illustrates a scenario where the drainage device of FIG. 1 is fixed in a bladder of a male by an inflatable balloon.

In addition, the drainage device 1 can be fixed in the bladder by a fixation structure, which can be an inflatable balloon, a pigtail structure, a V-shaped structure, a Malecot structure, a barbed structure, a deformable structure, a variable-size structure, or a friction structure. Please refer to FIG. 7, which illustrates a scenario where the drainage device of FIG. 1 is fixed in a bladder by an inflatable balloon 16 to provide an indwelling urinary drainage function. As for the drainage devices without the inflatable balloon 16, they can be used to provide an intermittent self-catheterization function.

Figure 8A:
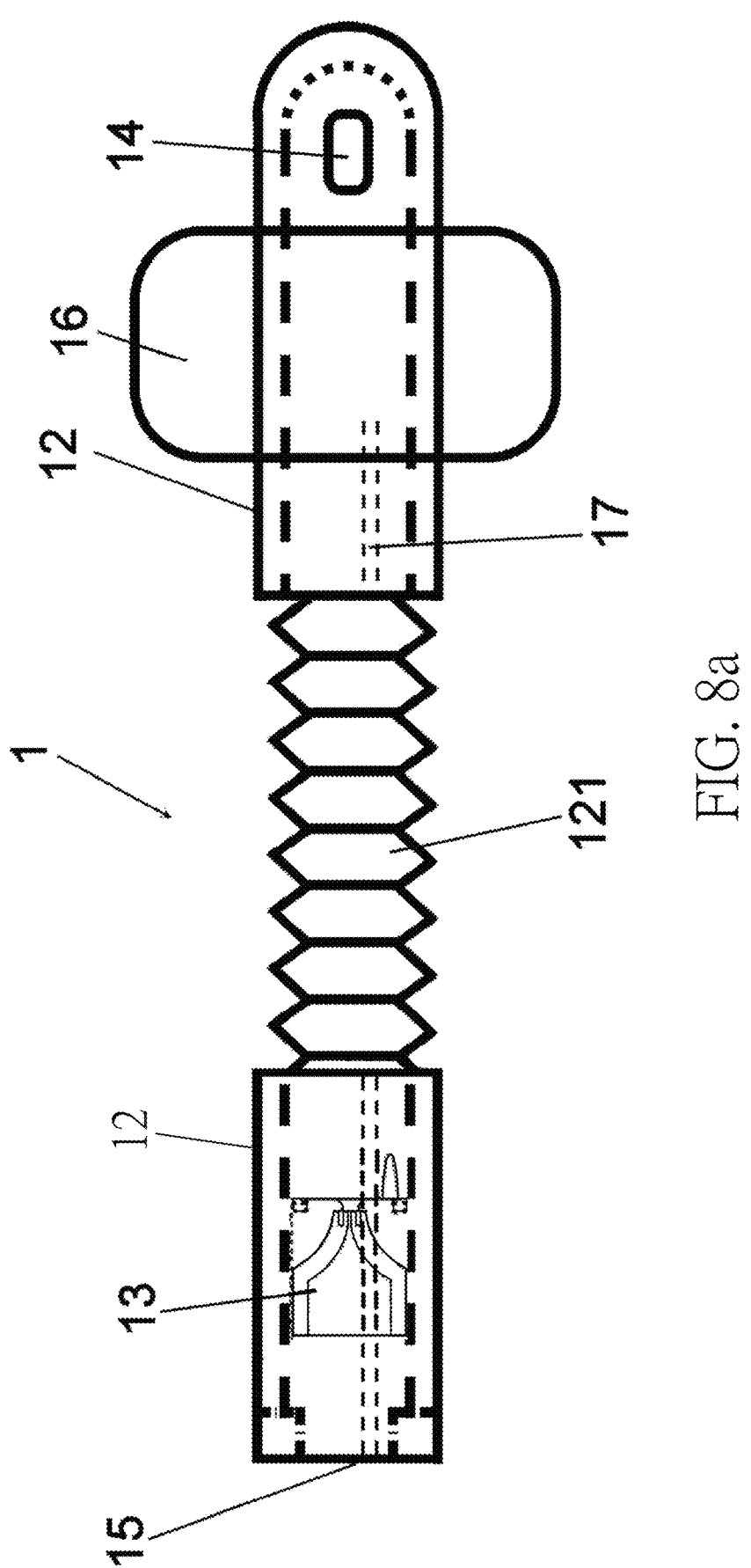
FIG. 8*a* shows an illustrative drawing of a drainage device according to another embodiment of the present invention, where a variable-length catheter is used.
Figure 8B:
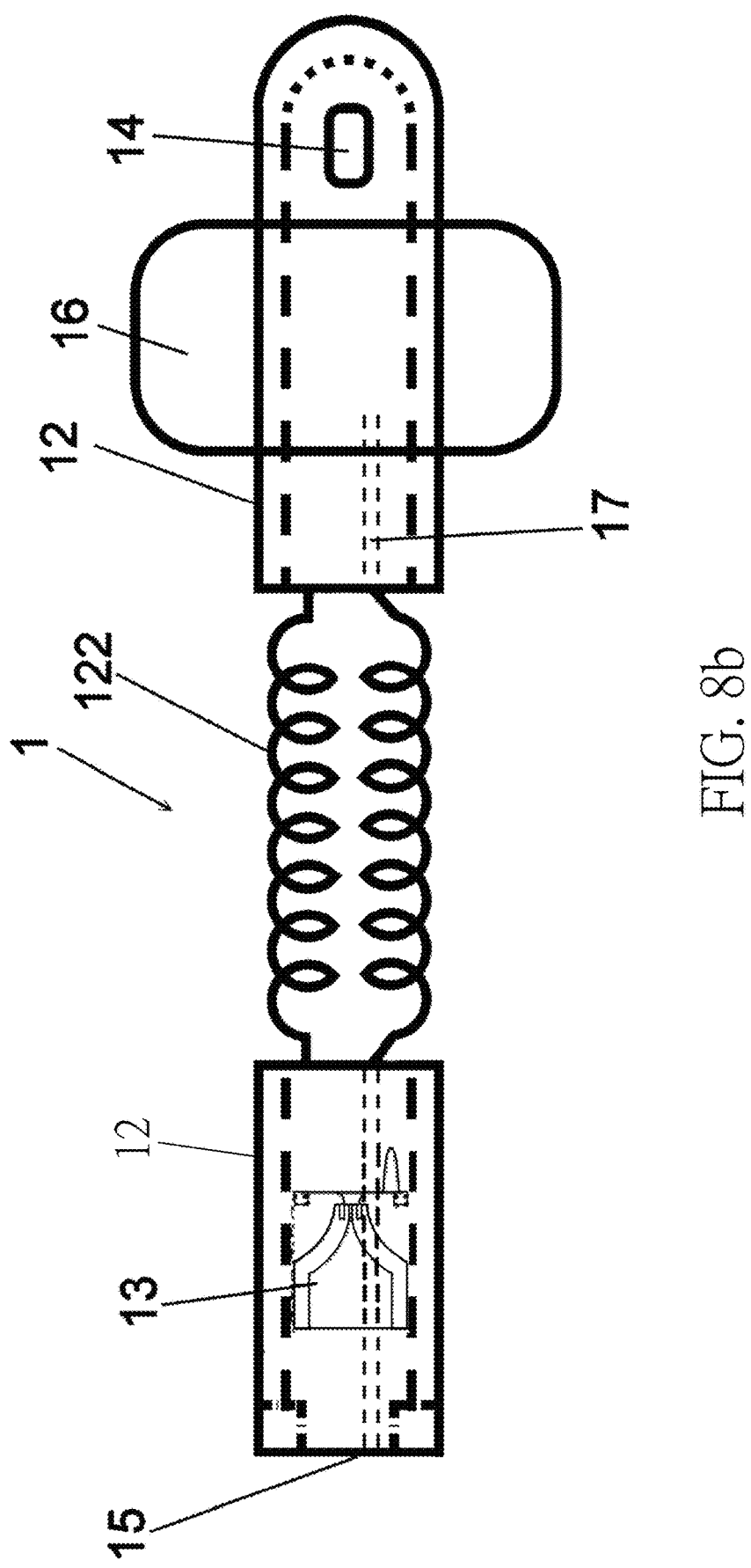
FIG. 8*b* shows an illustrative drawing of a drainage device according to another embodiment of the present invention, where another variable-length catheter is used.

In addition, the drainage device 1 can further include a variable-length channel section to adapt to the length of the penis at different statuses, especially at the erection status. Please refer to FIG. 8a and FIG. 8b, in which, FIG. 8a shows an illustrative drawing of a drainage device 1 having a first variable-length channel section 121 connected between two halves of the catheter 12, where the first variable-length channel section 121 has a central channel for the urine to flow through; and FIG. 8b shows an illustrative drawing of a drainage device 1 having a second variable-length channel section 122 connected between two halves of the catheter 12, where the second variable-length channel section 122 has a peripheral channel for the urine to flow through and can minimize the impact of the catheter 12 on the urinary sphincter function.

Figure 9:
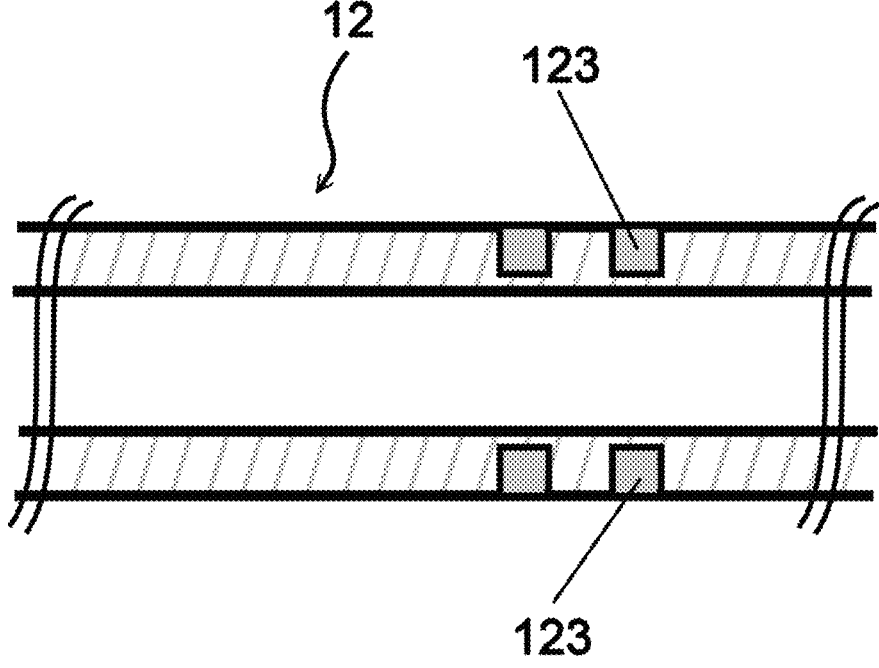
FIG. 9 illustrates a partial view of a catheter of a drainage device according to another embodiment of the present invention, where a ring-shaped slot is disposed on an outer surface of the shell of the catheter for drug storage.

In addition, as shown in FIG. 9, the catheter 12 of the drainage device 1 can further have a ring-shaped slot 123 disposed on an outer surface thereof for storing a drug, which can include an anti-sticking-to-skin agent, to simultaneously apply the drug when inserting the drainage device 1 into a cavity of a chamber.

Figure 10:
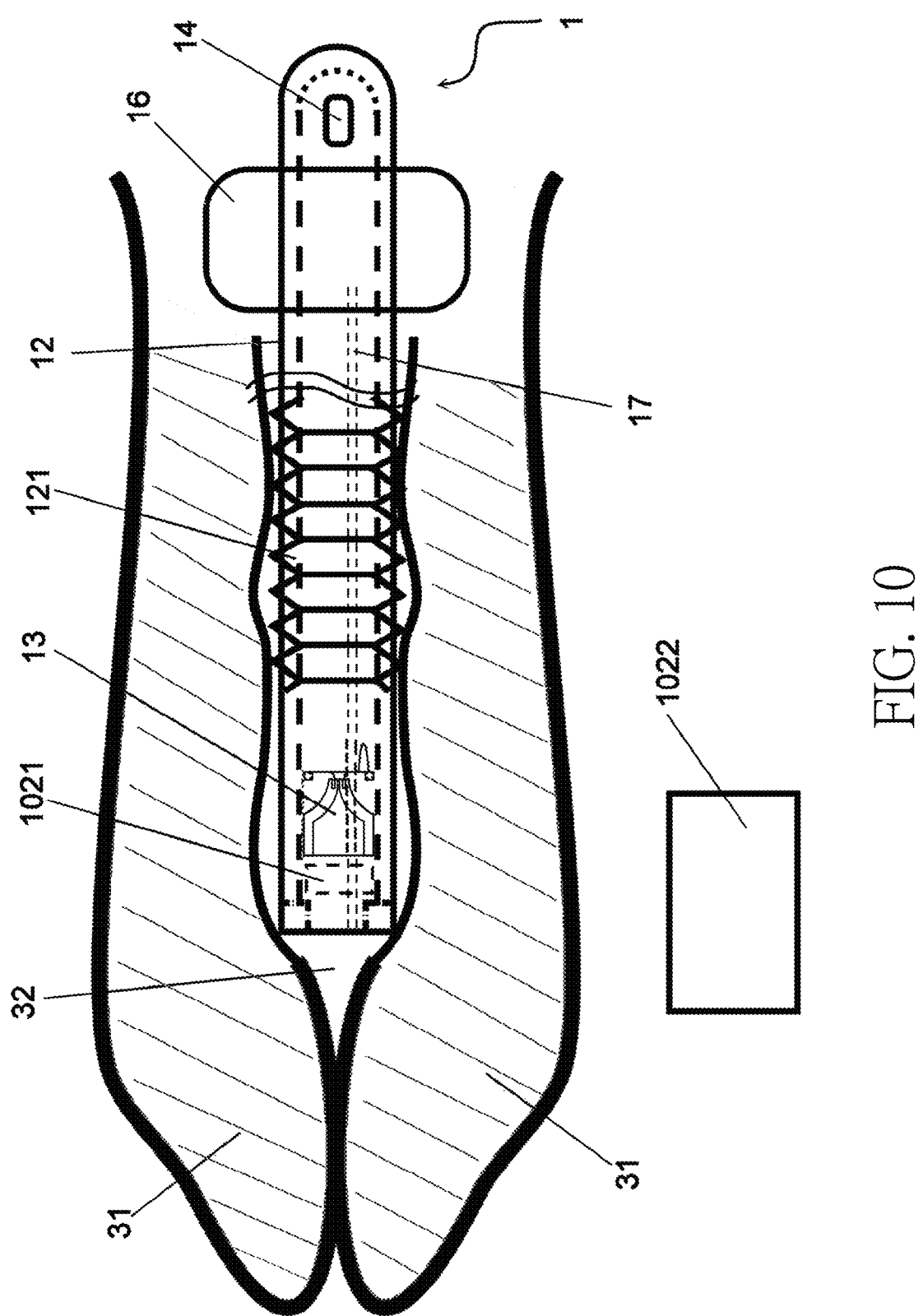
FIG. 10 illustrates a drainage device according to still another embodiment of the present invention, where the catheter is fixed in a penis under the control of an external control device.

In addition, as can be seen from FIG. 10, the drainage device 1 can be fixed in a penis 31 under the control of an external control device 1022. To be more specific, the drainage device 1 has a magnetic fixation device 1021 near the valve body 13 and being responsive to a magnetic force of the external control device 1022 to be fixed on spot. Besides, the external control device 1022 can also detect the position of the magnetic fixation device 1021 via the magnetic field thereof to enable medical personnel to conveniently implant or retrieve the drainage device 1.

As can be seen from the descriptions above, the invention discloses a drainage device including a catheter and a control valve connected with the catheter, characterized in that:

a) the control valve has a valve body and a resilient switch, the valve body having a passageway controlled by the resilient switch to be in a normally closed status, a normally open status, or a variable open status adjusted by a pressing force acting on the resilient switch;

b) the resilient switch includes an elastic structure, a driving part, a recovery-blocking part and an unlocking handle, where the driving part is movable by a deformation response of the elastic structure to have a displacement to alter an opening of the passageway of the valve body; the recovery-blocking part is used for providing a recovery-blocking effect on the driving part; and the unlocking handle is used for an external force to apply a moment of force on the driving part to release the recovery-blocking effect;

c) when the elastic structure is not pressed, the passageway is in a first normal status; when the elastic structure is under a press operation, the opening of the passageway is determined according to a relative relationship between the displacement and a displacement threshold, where, when the displacement is not larger than the displacement threshold, the passageway is in the variable open status, and the opening thereof is smaller than the opening of the normally open status, and when the displacement is larger than the displacement threshold, the driving part will be under the recovery-blocking effect provided by the recovery-blocking part to make the passageway situated in a second normal status, where when the first normal status is the normally closed status, the second normal status is the normally open status, and when the first normal status is the normally open status, the second normal status is the normally closed status; and d) after the passageway is in the second normal status, the unlocking handle can be used to release the recovery-blocking effect of the recovery-blocking part by applying the moment of force, thereby restoring the passageway to the first normal status.

In addition, to be more specific, the moment of force is generated by a bending operation or shaking operation acting on the catheter; the catheter is to be placed into a cavity to provide a flow controllable draining function; the catheter can have a fixation structure for fixing the catheter in the cavity, and the fixation structure can include at least one channel formed in a shell of the catheter and a balloon connected with the at least one channel, where the catheter is fixed in the cavity by introducing a volume of a fluid into the balloon via the at least one channel to inflate the balloon, where the fluid can be a gas or a liquid; the catheter can have an engagement structure disposed on an inner surface of the shell for fixing the elastic structure; the valve body can be a duckbill valve, a gate valve, a butterfly valve, a ball valve, a plunger valve, a plug valve or a diaphragm valve; the flow controllable draining function is for draining a body fluid in the cavity, and the body fluid can be urine.

Accordingly, the invention possesses the advantages as follows:

1. the drainage device of the invention not only allows a user to manually press a resilient switch hidden in a catheter to adjust the opening of the catheter, but also allows the user to perform a bending or shaking operation to release the resilient switch hidden in the catheter from a recovery-blocked status to make the resilient switch resiliently restored to an initial state;

2. the drainage device of the invention can offer an easy-to-operate flow controllable urinary drainage function for patients, especially for patients with urinary incontinence; and 3. the drainage device of the invention can offer an easy-to-operate flow controllable drainage function for post-surgery wounds.

What is claimed is:

1. A drainage device including a catheter and a control valve connected with the catheter, characterized in that:

the control valve has a valve body and a resilient switch, the valve body having a passageway controlled by the resilient switch to be in a normally closed status, a normally open status, or a variable open status adjusted by a pressing force acting on the resilient switch; and the resilient switch includes an elastic structure, a driving part, a recovery-blocking part and an unlocking handle, wherein the driving part is movable by a deformation response of the elastic structure to have a displacement to alter an opening of the passageway of the valve body; the recovery-blocking part is used for providing a recovery-blocking effect on the driving part; and the unlocking handle is used for an external force to apply a moment of force on the driving part to release the recovery-blocking effect;

wherein when the elastic structure is not pressed, the passageway is in a first normal status; when the elastic structure is under a press operation, the opening of the passageway is determined according to a relative relationship between the displacement and a displacement threshold, where, when the displacement is not larger than the displacement threshold, the passageway is in the variable open status, and the opening thereof is smaller than the opening of the normally open status, and when the displacement is larger than the displacement threshold, the driving part will be under the recovery-blocking effect provided by the recovery-blocking part to make the passageway situated in a second normal status, wherein when the first normal status is the normally closed status, the second normal status is the normally open status, and when the first normal status is the normally open status, the second normal status is the normally closed status; and wherein after the passageway is in the second normal status, the unlocking handle can be used to release the recovery-blocking effect of the recovery-blocking part by applying the moment of force, thereby restoring the passageway to the first normal status.

2. The drainage device as disclosed in claim 1, wherein the moment of force is generated by a bending operation or shaking operation acting on the catheter.

3. The drainage device as disclosed in claim 1, wherein the catheter is to be placed into a cavity to provide a flow controllable draining function.

4. The drainage device as disclosed in claim 3, wherein the catheter has a fixation structure for fixing the catheter in the cavity.

5. The drainage device as disclosed in claim 4, wherein the fixation structure includes at least one channel formed in a shell of the catheter and a balloon connected with the at least one channel, where the catheter is fixed in the cavity by introducing a volume of a fluid into the balloon via the at least one channel to inflate the balloon.

6. The drainage device as disclosed in claim 5, wherein the fluid is a gas or a liquid.

7. The drainage device as disclosed in claim 1, wherein the catheter has an engagement structure disposed on an inner surface of the shell for fixing the elastic structure.

8. The drainage device as disclosed in claim 1, wherein the valve body is selected from a group consisting of a duckbill valve, a gate valve, a butterfly valve, a ball valve, a plunger valve, a plug valve and a diaphragm valve.

9. The drainage device as disclosed in claim 3, wherein the flow controllable draining function is for draining a body fluid in the cavity.

10. The drainage device as disclosed in claim 9, wherein the body fluid is urine.

* * * * *